United States Patent
Koh

(10) Patent No.: US 7,869,878 B1
(45) Date of Patent: Jan. 11, 2011

(54) IMPLANTABLE CARDIAC STIMULATION DEVICE PROVIDING IEGM WITH REDUCED RESPIRATION MODULATION EFFECT AND METHOD

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 751 days.

(21) Appl. No.: 11/245,961

(22) Filed: Oct. 6, 2005

(51) Int. Cl.
*A61N 1/365* (2006.01)

(52) U.S. Cl. .................. 607/20; 607/18; 607/19; 600/513

(58) Field of Classification Search .............. 607/9, 607/19, 20, 42; 600/510, 513
See application file for complete search history.

(56) References Cited

U.S. PATENT DOCUMENTS

| | | | |
|---|---|---|---|
| 4,919,136 A * | 4/1990 | Alt | 607/20 |
| 5,735,284 A * | 4/1998 | Tsoglin et al. | 600/513 |
| 6,192,275 B1 * | 2/2001 | Zhu et al. | 607/28 |
| 6,449,509 B1 | 9/2002 | Park et al. | 607/20 |
| 6,697,672 B2 | 2/2004 | Andersson | 607/17 |
| 6,813,514 B1 | 11/2004 | Kroll et al. | 600/509 |
| 6,876,881 B2 * | 4/2005 | Baumann et al. | 607/18 |
| 6,881,192 B1 * | 4/2005 | Park | 607/17 |
| 7,025,729 B2 * | 4/2006 | de Chazal et al. | 600/508 |
| 2002/0095189 A1 | 7/2002 | Andersson | 607/25 |
| 2003/0171781 A1 * | 9/2003 | Florio et al. | 607/17 |
| 2004/0002741 A1 | 1/2004 | Weinberg | 607/17 |
| 2004/0138718 A1 * | 7/2004 | Limousin et al. | 607/17 |
| 2004/0158165 A1 * | 8/2004 | Yonce et al. | 600/510 |
| 2005/0004608 A1 | 1/2005 | Bullinga | 607/9 |
| 2005/0033368 A1 | 2/2005 | Fishler et al. | 607/9 |
| 2005/0137487 A1 * | 6/2005 | Zhu et al. | 600/513 |
| 2005/0148895 A1 * | 7/2005 | Misczynski et al. | 600/513 |
| 2006/0224074 A1 * | 10/2006 | Ouchi et al. | 600/513 |

FOREIGN PATENT DOCUMENTS

| EP | 1118307 A1 | 7/2001 |
|---|---|---|
| EP | 1192971 A2 | 1/2005 |

* cited by examiner

*Primary Examiner*—Scott M Getzow
*Assistant Examiner*—Joseph M Dietrich

(57) ABSTRACT

An implantable cardiac stimulation device provides an intracardiac electrogram with reduced respiratory modulation effect. The device includes a sensing circuit that senses cardiac activity and provides an intracardiac electrogram signal extending over a plurality of cardiac cycles, a respiration monitor that monitors respiration associated with the sensed cardiac activity, and a cardiac cycle selector that selects a set of intracardiac electrogram cardiac cycles of the plurality of cardiac cycles in response to the monitored respiration. A processing circuit processes the selected set of intracardiac electrogram cardiac cycles to provide the intracardiac electrogram with reduced respiratory modulation effect.

6 Claims, 3 Drawing Sheets

IMPLANTABLE CARDIAC STIMULATION DEVICE PROVIDING IEGM WITH REDUCED RESPIRATION MODULATION EFFECT AND METHOD

FIELD OF THE INVENTION

The present invention generally relates to an implantable cardiac stimulation device. The present invention more particularly relates to such a device that provides an intracardiac electrogram (IEGM) having reduced respiration modulation effect.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered to be comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied or intrinsic responses are sensed between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied or intrinsic responses are sensed between a pair of closely spaced electrodes carried by the lead, in electrical contact with the desired heart chamber, with the most proximal electrode serving as the anode and the most distal electrode serving as the cathode.

Pacemakers deliver pacing pulses to the heart to induce a depolarization and a mechanical contraction of that chamber when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

Recently, there has been the introduction of pacing systems that stimulate in corresponding chambers of the heart as, for example, the right ventricle (RV) and left ventricle (LV). These are termed biventricular stimulation devices.

Biventricular pacing has been shown to coordinate contractions of the left and right ventricles, reduce the amount of blood flow that leaks through the mitral valve, and decreases the motion of the septal wall that separates the chambers of the heart. Such motion can affect the quantity of blood that the ventricle can pump out in a single beat.

Biventricular pacing has been found to be particularly advantageous in patient's suffering from congestive heart failure (CHF) because of the improved ability of the left ventricle to fully pump blood from the heart. As a result, patients are able to tolerate greater exertion, have a longer life span, and experience a higher quality of life.

Congestive heart failure (CHF) is a debilitating, end-stage disease in which abnormal function of the heart leads to inadequate bloodflow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become leaky, allowing regurgitation or backflow of blood. The impairment of arterial circulation deprives vital organs of oxygen and nutrients. Fatigue, weakness, and inability to carry out daily tasks may result.

Not all CHF patients suffer debilitating symptoms immediately. Some may live actively for years. Yet, with few exceptions, the disease is relentlessly progressive.

As CHF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

Current standard treatment for heart failure is typically centered around medical treatment using ACE inhibitors, diuretics, and digitalis. It has also been demonstrated that aerobic exercise may improve exercise tolerance, improve quality of life, and decrease symptoms. Only an option in 1 out of 200 cases, heart transplantation is also available. Other cardiac surgery is also indicated for only a small percentage of patients with particular etiologies. Although advances in pharmacological therapy have significantly improved the survival rate and quality of life of patients, patients who are refractory to drug therapy, have a poor prognosis and limited exercise tolerance.

Cardiac pacing is now considered a primary treatment for patients with drug-refractory CHF. By tracking the progression or regression of the heart disease more closely, stimulation therapy could be managed more effectively. Hence, it would be advantageous if the implanted cardiac stimulation device were able to aid in the tracking of the progression or regression of the heart disease.

One method of tracking a patient's CHF condition relies upon intracardiac electrogram (IEGM) morphology. From IEGM's saved over time, CHF surrogate parameters may be extracted which indicate the progression or regression of the CHF disease. Unfortunately, IEGM's are generally modulated by the patient's respiration. Such respiration modulation interferes with the parameter extractions. Hence, it would be desirable to be able to generate IEGM's which have reduced respiration modulation effect. The present invention addresses these and other issues.

SUMMARY

What is described herein is an implantable cardiac stimulation device including a system that generates an intracardiac electrogram with reduced respiratory modulation effect. The system comprises a sensing circuit that senses cardiac activity and provides an intracardiac electrogram signal extending over a plurality of cardiac cycles, a respiration monitor that monitors respiration associated with the sensed cardiac activity, a cardiac cycle selector that selects a set of intracardiac electrogram cardiac cycles of the plurality of cardiac cycles in response to the monitored respiration, and a processing circuit that processes the selected set of intracardiac electrogram cardiac cycles to provide the intracardiac electrogram with reduced respiratory modulation effect.

The respiration monitor may comprise an integrator that integrates the intracardiac electrogram signal to reveal a respiration pattern having at least one cycle. The cardiac cycle selector selects a set of cardiac cycles occurring during a complete respiratory cycle of the respiration.

The cardiac cycle selector may select the set of cardiac cycles occurring during a complete respiratory cycle of the respiration by terminating the cardiac activity sensing after completion of the respiratory cycle.

The processing circuit may comprise an averaging circuit that averages the selected set of intracardiac electrogram cardiac cycles to provide the intracardiac electrogram free of respiratory modulation. The system may further comprise a memory that stores the intracardiac electrogram free of respiratory modulation.

The implantable cardiac stimulation device may include a pulse generator that provides pacing pulses on demand pursuant to pacing parameters. The system may further comprise a parameter control that sets temporary pacing parameters for use by the pulse generator during the sensing of the cardiac activity over the plurality of cardiac cycles. The parameter control may further restore permanent pacing parameters for use by the pulse generator after the plurality of cardiac cycles.

The cardiac stimulation device may further include an activity sensor that senses patient activity. The sensing circuit may begin the sensing of cardiac activity after the activity sensor senses at rest patient activity. The at rest patient activity is preferably sleep activity.

In another embodiment, an implantable cardiac stimulation device generates an intracardiac electrogram having reduced respiratory modulation effect. The device comprises a pulse generator that provides pacing pulses to a heart on demand, a sensing circuit that senses cardiac activity and provides an intracardiac electrogram signal extending over a plurality of cardiac cycles, a respiration monitor that monitors respiration associated with the sensed cardiac activity, a cardiac cycle selector that terminates the cardiac activity sensing in response to one or more complete number of respiratory cycles monitored by the respiration monitor, and a processing circuit that processes the plurality of intracardiac electrogram cardiac cycles to provide the intracardiac electrogram having reduced respiratory modulation effect.

In yet another embodiment, a method of providing an intracardiac electrogram having reduced respiratory modulation effect is provided. The method comprises sensing cardiac activity to generate an intracardiac signal over a plurality of cardiac cycles, monitoring a respiratory pattern associated with the intracardiac signal, selecting a set of intracardiac signal cardiac cycles responsive to the respiratory pattern, and processing the selected set of intracardiac signal cardiac cycles.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
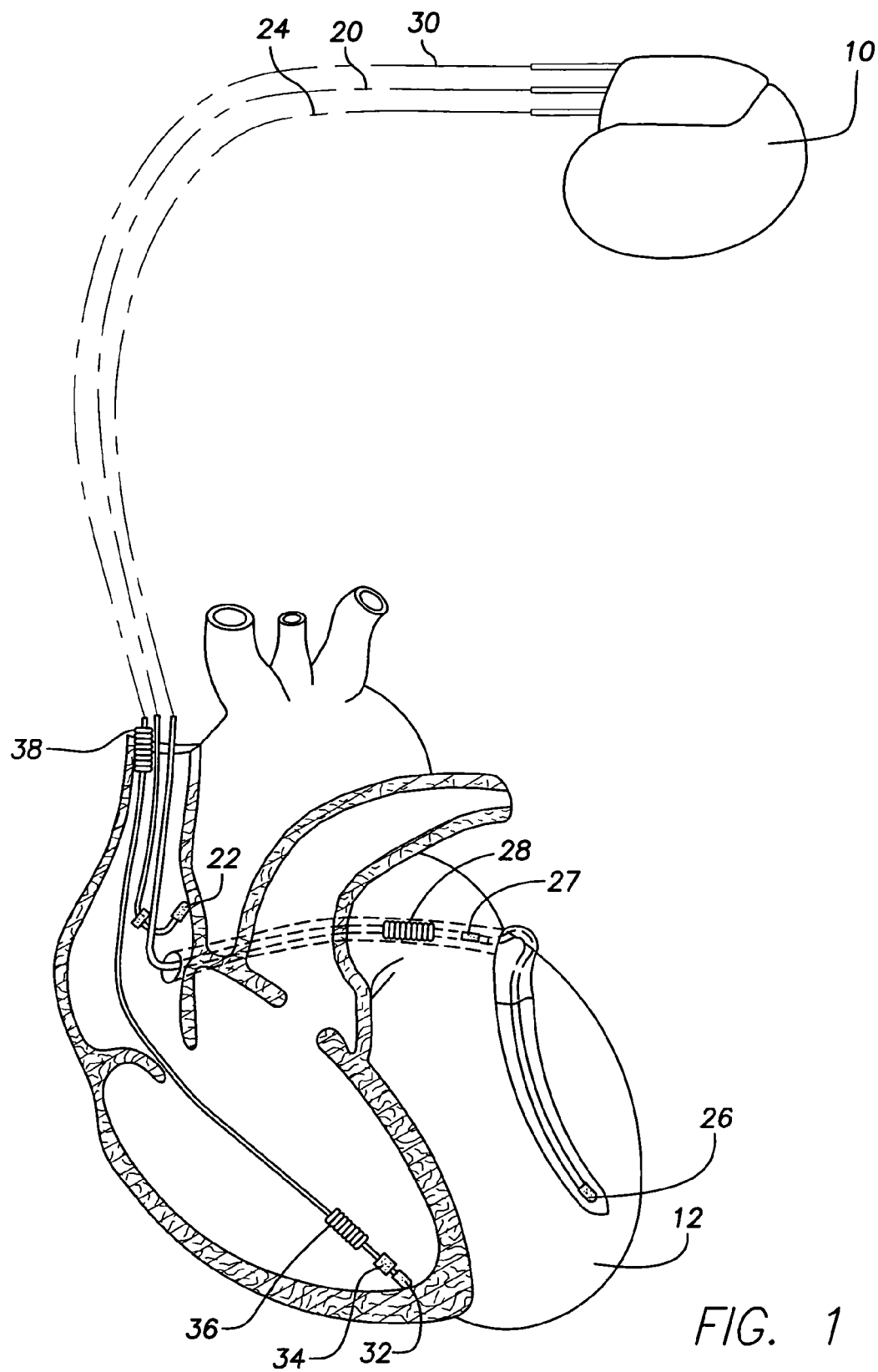
FIG. 1 is a simplified diagram illustrating an implantable stimulation device according to an embodiment of the invention having at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
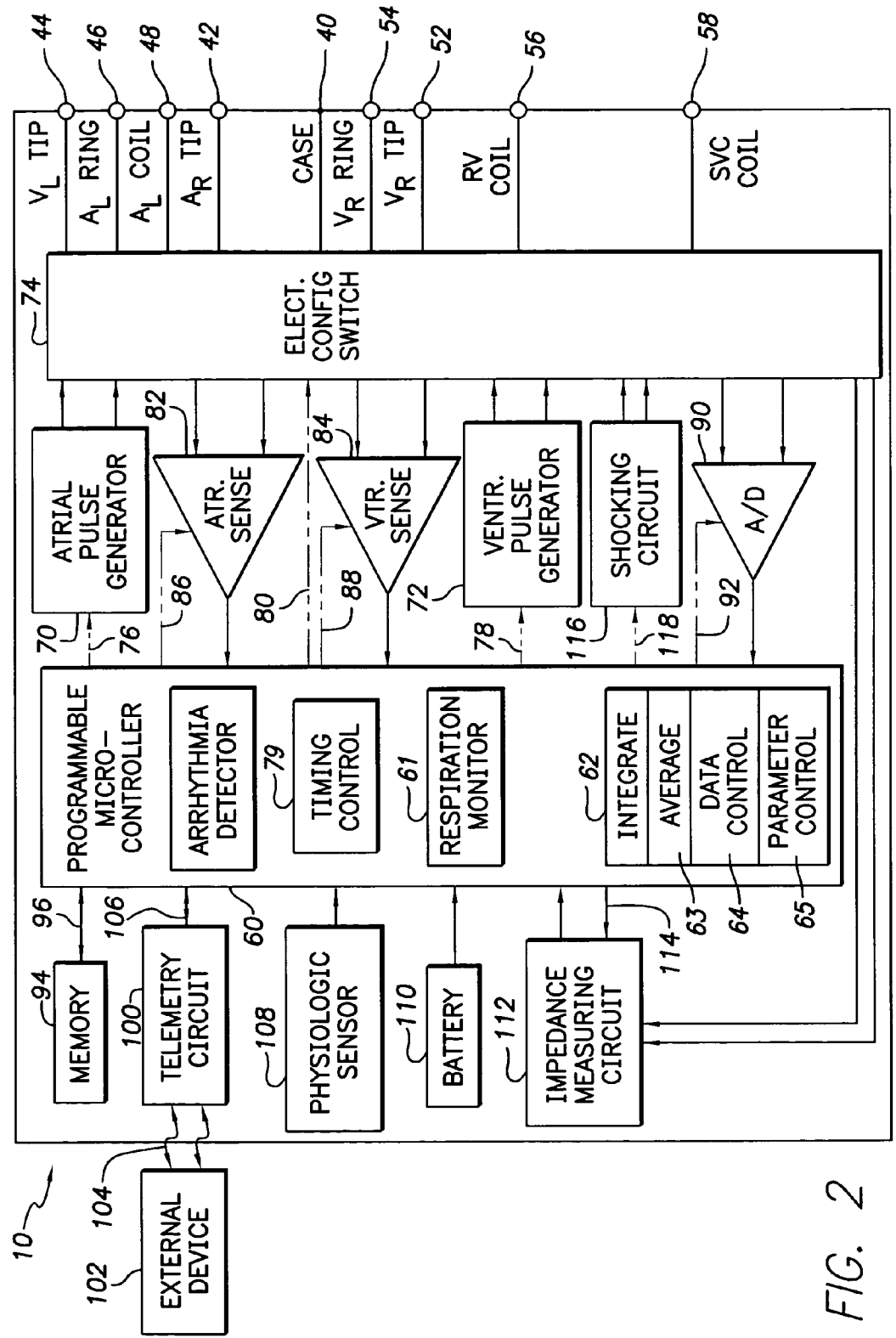
FIG. 2 is a functional block diagram of the multi-chamber implantable stimulation device of FIG. 1 illustrating the basic elements thereof to provide cardioversion, defibrillation and pacing stimulation in four chambers of the heart as well as the generation of IEGM's having reduced respiration modulation effect according to an embodiment of the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes. As will be seen subsequently, the data acquisition system may be used to acquire IEGM's in the provision of an IEGM devoid of respiration modulation according to an embodiment of the present invention.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries, as are known in the art.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

According to this embodiment of the present invention, the device 10 provides a cardiac cycle of an intracardiac electrogram (IEGM) that has reduced respiration modulation effect. To that end, the device 10 further includes a respiration monitor 61, an integrator 62, an averager 63, a data control 64, and a parameter control 65.

The respiration monitor 61 develops a respiration pattern from the IEGM's developed by the data acquisition system 90. To develop the respiration patterns, the respiration monitor. 61 utilizes the integrator 62 for integrating each cardiac cycle of IEGM acquired by the data acquisition system 90. Such a respiration pattern is shown in FIG. 3.

Figure 3:
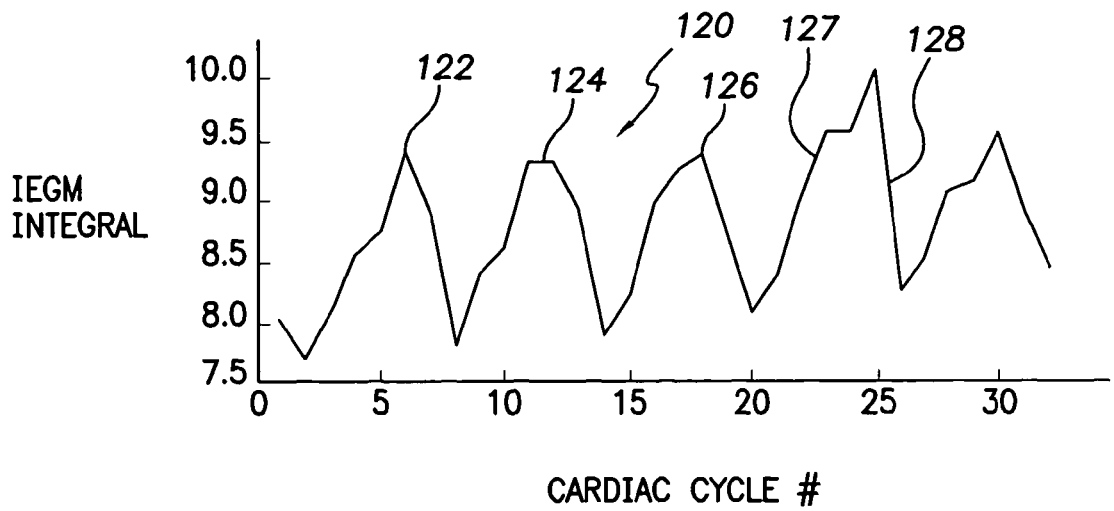
FIG. 3 is a plot of integrated IEGM cardiac cycles versus cardiac cycle number in accordance with one embodiment of the present invention.

In FIG. 3, a plot is shown of the integrated IEGM cardiac cycles versus the cardiac cycle number providing the IEGM integration value. As may be noted from FIG. 3, there is a definite respiration pattern developed from the integrals of the IEGM cardiac cycles. Of particular note are the complete cycles in the respiration pattern 120. More specifically, the IEGM integrals from peak 122 to peak 124 is one complete respiration pattern cycle. Similarly, another respiration pattern cycle runs from peak 124 to peak 126. Similarly, a complete respiration pattern cycle may be taken from integration value 127 to integration value 128.

The respiration pattern of FIG. 3 may be utilized to advantage according to this embodiment to permit the correct number of IEGM cardiac cycles to be averaged which will result in the respiratory modulation being cancelled out. More specifically, according to this embodiment, during the generation of an IEGM signal, a respiration pattern similar to that shown in FIG. 3 is developed. The cardiac cycles of IEGM which are produced during one or more complete respiratory cycles are then averaged after collection to derive a single cardiac cycle IEGM which is devoid of respiratory modulation. Of course, during the generation of the IEGM, less than all of the cardiac cycles may be selected for averaging. As a result, the selected IEGM cardiac cycles may be considered a selected set of cardiac cycles from the IEGM cardiac cycles generated.

Referring again to FIG. 2, the averager 63 may be utilized to average the selected IEGM cardiac cycles. The averager may be of the type known in the art wherein the IEGM cardiac cycles to be averaged are aligned per ventricular pacing pulse so that corresponding data points from each IEGM cardiac cycle may be averaged to result in an averaged IEGM cardiac cycle. The data control 64 may be utilized to select the IEGM cardiac cycles to be averaged as will be described hereinafter.

The parameter control 65 may be employed to set a particular set of pacing operating parameters to be utilized during the generation of the IEGM signal. For example, the parameter control 65 may establish pacing parameters during the gathering of the IEGM's so that uniform pacing conditions will prevail. This is provided as a result of the contemplation that a number of averaged IEGM cardiac cycles may be required for the eventual extraction of the CHF status parameters. For example, an averaged IEGM cardiac cycle devoid of respiration modulation may be provided each day over a 180 day period. The averaged IEGM cardiac cycles may be stored, for example, in a circular buffer of memory 94. Once the required number of averaged IEGM cardiac cycles are stored, they may be transmitted from the memory 94 to an external device 102, such as an external programmer, by the telemetry circuit 100. The external device 102 may then extract the CHF surrogate parameters from the morphology of the averaged IEGM cardiac cycles.

Hence, the parameter control 65 assures that the pacing conditions under which the IEGM data is collected are uniform for each data collection. The parameters which may be set to that end include the AV delay, V-V interval, pacing amplitude/duration, and ventricular blanking period of a shortened duration of, for example, 17 milliseconds. Also, it is preferable that only the cardiac cycles occurring during one complete respiration cycle be utilized for the IEGM averaging to minimize the number of cardiac cycles under which the pacing parameters are thus controlled.

Figure 4:
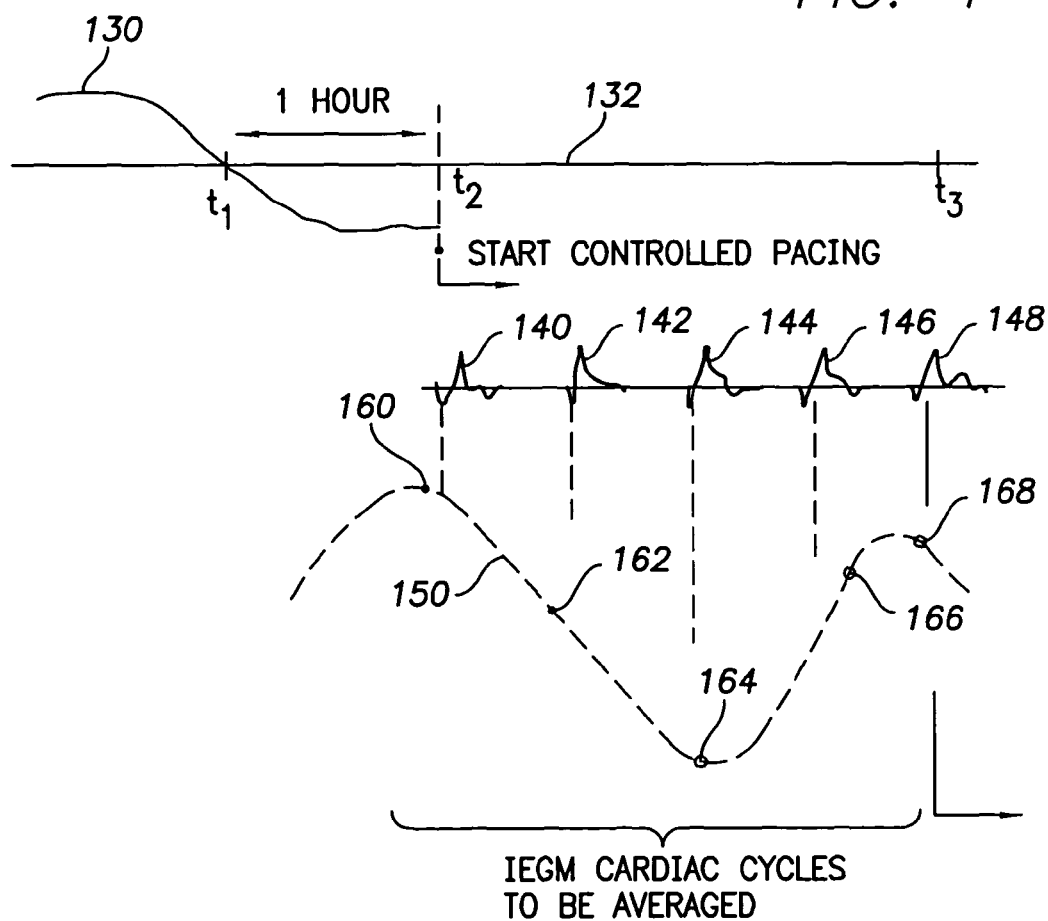
FIG. 4 is a time line illustrating a manner in which IEGM cardiac cycles may be selected for use in providing an IEGM having reduced respiration modulation effect according to an embodiment of the present invention.

FIG. 4 shows a simplified timeline indicating the process steps according to this embodiment which may be performed to collect the appropriate number of IEGM cardiac cycles for averaging. As will be noted in FIG. 4, the activity of the patient is denoted by the line 130 which may be, for example, the output of the accelerometer sensor 108 (FIG. 2). When the activity level of the patient reaches a sleep threshold 132 at time $T_1$, the timing control 79 may start the timing of a predetermined time period of, for example, one hour set to end at $T_2$. After the one hour time period ending at time $T_2$, the parameter control 65 may set the pacing parameters to the temporary default values for use during the IEGM collection beginning at time $T_2$. During the collection of the IEGM cardiac cycles 140, 142, 144, 146, and 148, the respiration monitor 61 develops the respiration pattern 150. More specifically, after each cardiac cycle of IEGM is stored, the integral under the IEGM for each cardiac cycle is determined by the integrator 62. As a result, the integral of cardiac cycle 140 is represented by the integral value 160. Similarly, the integral of the cardiac cycle 142 is represented by the integral value 162. The integrals of the remaining cardiac cycles 144, 146, and 148, are represented by the integral values 164, 166, and 168, respectively. Hence, as will be noted, the integral values result in the respiration pattern 150. Of particular note is that the pattern 150 from the integral value 160 to the integral value 168 comprises a full cycle of the respiration pattern 150. As a result, the cardiac cycles 140, 142, 144, 146, and 148 are selected and used for the IEGM cardiac cycle averaging to provide an IEGM cardiac cycle which is devoid of respiration modulation. Once it is determined that a complete respiration cycle has occurred, the pacing parameters may be returned to the patient's permanent pacing parameter values at time $T_3$.

Once the IEGM cardiac cycles 140, 142, 144, 146, and 148 are averaged, the resulting averaged IEGM cardiac cycle will have a reduced respiration modulation effect. The averaged IEGM cardiac cycle may be stored in memory 94. At the appropriate time, such as during a follow-up visit by the patient, the stored averaged IEGM cardiac cycle, along with other such averaged IEGM cardiac cycles, may be transmitted to the external device 102. From the averaged IEGM cardiac cycles the external device 102 may extract the CHF surrogate parameters.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device that generates an intracardiac electrogram having reduced respiratory modulation effect, comprising:
   a pulse generator that provides pacing pulses to a heart;
   a sensing circuit that senses cardiac activity evoked by pacing pulses provided in accordance with temporary pacing parameters and provides an intracardiac electrogram (IEGM) signal extending over a plurality of cardiac cycles, wherein the IEGM signal corresponds to the cardiac activity evoked by the pacing pulses;
   an integrator configured to receive the IEGM signal from the sensing circuit and to determine the integral under each cardiac cycle in the IEGM signal;
   a respiration monitor configured to monitor the determined integrals and determine when one or more complete respiratory cycles have occurred based on the determined integrals;
   a cardiac cycle selector configured to select a set of IEGM cardiac cycles from the IEGM signal that occurred during the time of the one or more complete respiratory cycles determined by the respiration monitor;
   a processing circuit configured to process the selected set of IEGM cardiac cycles to provide the IEGM having reduced respiratory modulation effect; and
   a controller that controls the pulse generator to provide pacing pulses in accordance with the temporary pacing parameters, and once it is determined that one or more complete respiratory cycles has occurred, to provide pacing pulses in accordance with permanent pacing parameters.

2. The device of claim 1, wherein the cardiac cycle selector terminates the cardiac activity sensing after one complete respiratory cycle.

3. The device of claim 1, wherein the processing circuit comprises an averaging circuit that averages the selected set of intracardiac electrogram cardiac cycles to provide the intracardiac electrogram having reduced respiratory modulation effect.

4. The device of claim 1, further comprising a memory that stores the intracardiac electrogram having reduced respiratory modulation effect.

5. The device of claim 1, further comprising an activity sensor that senses patient activity and wherein the controller controls the pulse generator to provide pacing pulses in accordance with the temporary pacing parameters after the activity sensor senses at rest patient activity.

6. The device of claim 5, wherein the at rest patient activity is sleep activity.

* * * * *